US010080364B2

(12) United States Patent
Shroff et al.

(10) Patent No.: US 10,080,364 B2
(45) Date of Patent: Sep. 25, 2018

(54) SELECTIVE WEED CONTROL USING D-NAPROPAMIDE

(71) Applicant: UPL LIMITED, Mumbai (IN)

(72) Inventors: Jaidev Rajnikant Shroff, Mumbai (IN); Vikram Rajnikant Shroff, Mumbai (IN); Jean-Jacques Heller, Courbevoie (FR)

(73) Assignee: UPL Limited, Mumbai (IN)

( * ) Notice: Subject to any disclaimer, the term of this patent is extended or adjusted under 35 U.S.C. 154(b) by 19 days.

(21) Appl. No.: 15/094,397

(22) Filed: Apr. 8, 2016

(65) Prior Publication Data

US 2016/0219877 A1    Aug. 4, 2016

Related U.S. Application Data

(63) Continuation of application No. 13/839,979, filed on Mar. 15, 2013, now Pat. No. 9,307,765.

(51) Int. Cl.

| | | |
|---|---|---|
| *A01N 39/02* | (2006.01) | |
| *A01N 37/22* | (2006.01) | |
| *A01N 43/80* | (2006.01) | |
| *A01N 37/20* | (2006.01) | |
| *A01N 43/40* | (2006.01) | |
| *A01N 43/42* | (2006.01) | |
| *A01N 43/58* | (2006.01) | |
| *A01N 43/707* | (2006.01) | |
| *A01N 43/78* | (2006.01) | |
| *A01N 43/90* | (2006.01) | |
| *A01N 47/20* | (2006.01) | |
| *A01N 47/32* | (2006.01) | |
| *A01N 57/20* | (2006.01) | |

(52) U.S. Cl.
CPC ............ *A01N 37/20* (2013.01); *A01N 37/22* (2013.01); *A01N 39/02* (2013.01); *A01N 43/40* (2013.01); *A01N 43/42* (2013.01); *A01N 43/58* (2013.01); *A01N 43/707* (2013.01); *A01N 43/78* (2013.01); *A01N 43/80* (2013.01); *A01N 43/90* (2013.01); *A01N 47/20* (2013.01); *A01N 47/32* (2013.01); *A01N 57/20* (2013.01)

(58) Field of Classification Search
None
See application file for complete search history.

(56) References Cited

U.S. PATENT DOCUMENTS

| | | |
|---|---|---|
| 3,718,455 A | 2/1973 | Baker et al. |
| 5,583,090 A | 12/1996 | Stern et al. |
| 5,783,520 A | 7/1998 | Anderson et al. |
| 6,677,276 B1 * | 1/2004 | Hacker .................. A01N 57/20 504/127 |
| RE38,675 E | 12/2004 | Lee et al. |
| 8,307,765 B2 * | 11/2012 | Orlandi ..................... B32B 5/26 101/484 |
| 8,309,765 B2 | 11/2012 | Shroff et al. |

FOREIGN PATENT DOCUMENTS

| | | | | |
|---|---|---|---|---|
| WO | 2009/004642 A2 | 1/2009 | | |
| WO | WO-2009004642 A2 * | 1/2009 | ........... | C07C 231/12 |
| WO | 2011/121407 A1 | 10/2011 | | |

OTHER PUBLICATIONS

Santos(Drip-applied metam potassium and herbicides as methyl bromide alternatives for Cyperus control in tomato, Crop Protection (2009), vol. 28, No. 1, pp. 68-71) (Year: 2009).*
Willoughby et al.( Tolerance of broadleaved tree and shrub seedlings to preemergence herbicides, New Forests (2007), vol. 34, No. 1, pp. 1-12, 25) (Year: 2007).*
Wilcox-Lee et al.( Tillagereduces yield and crown, fern, and bud growth in a mature asparagus planting, Journal of the American Society for Horticultural Science (1991), vol. 116, No. 6, pp. 937-941) (Year: 1991).*
Sieczka et al.( Proceedings 39th annual meeting of the Northeastern Weed Science Society. (1985), pp. 134-135) (Year: 1985).*
Bielenin ( Efficacy and phytotoxicity of several herbicides in mature container-grown conifers, Zeszyty Naukowe Instytutu Sadownictwa i Kwiaciarstwa w Skierniewicach (2003), vol. 11, pp. 179-186).*
Toth et al.( Activated carbon improves the tolerance of lettuce to mixtures of napropamide with diuron or prometryne , Proceedings II of the 10th Australian Weeds Conference and 14th Asian Pacific Weed Science Society Conference, Brisbane, Australia, Sep. 6-10, 1993 (1993), pp. 52-7).*
Elmstrom ( Weed control for commercial vegetable production, Annual Research Report of the Institute of Food and Agricultural Sciences, University of Florida, Gainesville, 1974. (1976), pp. 402-403).*
O'Sullivan et al. ( Weed control in transplanted cabbage, Res.Rep. Expert Comm.Weeds East.Can. (40 Meet., vol. 2, 719-20, 1995) 1 Tab).*
Hamill ( Annual Weed Control for Standard Row Seeded Cucumbers. Annual Weed Control for 30cm Row Seeded Cucumbers, Res.Rep.Expert Comm.Weeds East.Can. (33 Meet., vol. 1, 430-31, 1989, 2 Tab.).*
O'Sullivan et al. ( Weed control in transplanted peppers, Res.Rep. Expert Comm.Weeds East.Can. (31 Meet., vol. 1, 511, 1987) 1 Tab. (AJU)).*

* cited by examiner

*Primary Examiner* — Alton N Pryor
(74) *Attorney, Agent, or Firm* — Wiley Rein LLP

(57) ABSTRACT

The present invention provides a novel use of D-Napropamide and a method comprising the use of D-Napropamide and combinations comprising the same.

20 Claims, No Drawings

SELECTIVE WEED CONTROL USING D-NAPROPAMIDE

RELATED APPLICATIONS

This application is a continuation of U.S. patent application Ser. No. 13/839,979, filed Mar. 15, 2013, now U.S. Pat. No. 9,307,765, which is incorporated herein by reference for all purposes.

FIELD OF INVENTION

The present invention relates to the use of Napropamide-M for selective control of dicotyledonous weeds.

BACKGROUND AND PRIOR ART

Many herbicides are reported in the prior art. However, the herbicidal effectiveness of a given compound cannot be predicted from an examination of the substituent groups of the compound and often quite closely related compounds, which will have quite different weed control abilities. Various herbicides or the isomers of the same herbicide may have overlapping or complementary areas of activity or selectivity, and can thus be useful to control a variety of weeds upon application of a composition. Furthermore, the various known herbicides are not completely effective. An ideal herbicide should give selective weed control, over the full growing season, with a single administration. It should be able to control all common weeds by controlling their growth and reproduction as the seed, the germinating seed, the seedling, and the growing plant.

Although the enantiomers of chiral substances have the same physicochemical properties, their biochemical activities can be quite different because biochemical processes usually show high stereo- or enantioselectivity.

The "active" enantiomer of a chiral chemical may have the desired effect on a target species, whereas the other enantiomer may not. It is advisable to use only the biologically active enantiomers, thereby reducing the total amount of chemical pollutants released into the environment.

Many agrochemicals have chiral structures. For example, about 30% of currently registered pesticide active ingredients contain one or more chiral centers. Herbicides are used to control the growth of undesired vegetation, and they account for most of the agrochemicals in use today. Some chiral herbicides are sold as purified, optically active isomers, but for economic reasons, many others are still used as racemates. Different enantiomers of chiral herbicides can have different enantioselective activities on target weeds and different toxic effects on non-target organisms because of their enantioselective interactions with enzymes and biological receptors in organisms but the herbicidal selectivity of a specific isomer is not predictable.

N,N-diethyl-2-(α-naphthoxy)propionamide is known as napropamide, and its racemic mixture is generally marketed under trade name as DEVRINOL® (napropamide). It is used for pre-emergence control of annual grasses and broad-leaved weeds in many crops and plantations.

The second carbon atom at the propionamide group in napropamide has a hydrogen atom, a methyl group, a naphthoxy moiety and a carboxamide group thereby forming a chiral center. Hence the molecule can exist in two chiral stereoisomers: D or (R) and L or (S)-isomers:

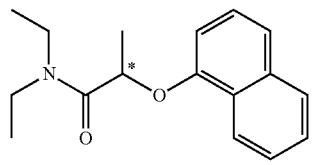 [SMILES: CCN(CC)C(=O)C(C)Oc1cccc2ccccc12]

Napropamide is a selective systemic herbicide absorbed by roots and translocated acripetally. It inhibits root development and growth.

Unsolved problems in this area include widely differing sensitivities of crop plants against herbicidal chemicals as well as the fact that repression of one weed species may cause increased growth of another competing weed species, and that some weeds tend to become resistant against previously effective herbicides.

U.S. Pat. No. 3,718,455 discloses new organic compounds of formula I used as herbicides:

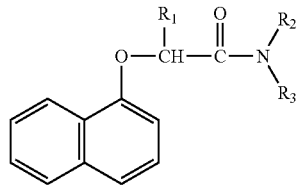

This structure includes the compound Napropamide (Compound No. 54 and Compound No. 55). The herbicidal activity of compounds 1 to 22 is reported on crabgrass, annual bluegrass, watergrass and foxtail. This patent discloses that Compound No. 54 and Compound No. 55 possess good herbicidal activity and can be used as pre-emergent and post-emergent herbicides (Table III). This patent disclosure did not investigate and does not indicate any differential selectivity of D-Napropamide towards different weed classes or types.

WO2009004642 discloses a process for manufacture of high purity D-(−)-N,N-diethyl-2-(α-naphthoxy)propionamide from L-2-Halopropionic Acid or (s)-(−)-2-Halopropionic Acid and composition comprising high purity D-(−)-N,N-diethyl-2-(α-naphthoxy)propionamide. Again, this patent disclosure did not investigate and does not indicate any differential selectivity of D-Napropamide towards different weed classes or types.

There is a need in the art for enhanced uses of D-Napropamide and for improved methods of herbicidal control by using D-Napropamide.

SUMMARY OF THE INVENTION

In one aspect, the present invention provides the use of D-Napropamide for selective control of dicotyledonous weeds at a locus.

In another aspect, the present invention provides a method of selectively controlling dicotyledonous weeds infestation at a locus by treating said locus with a herbicidally effective amount of D Napropamide.

In yet another aspect, the present invention provides a herbicidal composition for selectively controlling the dicotyledonous weeds infestation at a locus, said composition comprising D-Napropamide.

DETAILED DESCRIPTION OF THE INVENTION

In this specification, the terms Napropamide-M and D-Napropamide are used interchangeably.

Racemic Napropamide has a satisfactorily good herbicidal activity. D-Napropamide possesses improved activity than L-Napropamide. A comparatively similar distribution of herbicidal activity enhancement by use of D-Napropamide (over racemic Napropamide) for monocotyledonous weeds as well as dicotyledonous weeds was expected. It was surprisingly found that D-Napropamide demonstrates a selectively enhanced control in the growth of dicotyledonous weeds in agronomic crops vis-à-vis the control in monocotyledonous weeds.

Therefore, in an embodiment, the present invention provides use of D-Napropa-mide for the control of a dicotyledonous weed at a locus. Typically, the D-Napropamide is used for selective control of said dicotyledonous weed.

The term locus as used herein shall denote the vicinity of a desired crop in which weed control, typically selective weed control, of dicotyledonous weeds is desired. The locus includes the vicinity of desired crop plants wherein the weed infestation has either emerged or is yet to emerge. The term crop shall include a multitude of desired crop plants or an individual crop plant growing at a locus.

The term control indicates eradication of the investigated weed(s). A 100% control signifies total eradication of the weed(s) under investigation.

In another embodiment, the present invention provides a method of controlling dicotyledonous weeds infestation at a locus by treating said locus with a herbicidally effective amount of D-Napropamide.

Preferably, treating the locus with D-Napropamide comprises administering to the soil in which the desired crop is to be planted, an effective amount of D-Napropamide. The administration is preferably by application either before seeding, during seeding, or, as in most applications, after seeding and before the crop emerges, so as to prevent the emergence of any weeds.

In an embodiment, D-Napropamide is administered prior to the emergence of any weed.

Among the crops which show pre-emergence tolerance to D-Napropamide and in which this compound can be used as a herbicide are winter oilseed rape, strawberries, blackcurrants, gooseberries, raspberries, field trees, shrubs, broccoli, cabbage, calabrese, cauliflower, kale and Brussel's sprouts. The method of the present invention is particularly useful in controlling the growth of dicotyledonous weeds in these crops.

In an embodiment, the dicotyledonous weeds which were found surprisingly susceptible to D-Napropamide are selected from the group comprising chickweed, speedwell, poppy, field bindweed, hairy fleabane, nettleaf goosefoot, common groundsel, horseweed, common lambsqaurters, little mallow, burning nettle, sowthistles, carpetweed, fat hen, blackberry nightshade, small flowered mallow, nettles, deadnettle, knotweed, common sowthistle, and *amaranthus*.

However, it should be understood that the use of D-Napropamide and a method of the present invention is not limited to the control of these weeds alone but is applicable to any dicotyledonous weed.

The herbicide of the invention can be applied to the soil or to crops in any amount which will give the required control of weeds. A preferred rate of application is from about 0.5 to about 20 L/Ha of D Napropamide, and most preferably from about 1 to about 8 L/Ha.

In an embodiment, Napropamide-M may be preferably used for control of dicotyledonous weeds in oil-seed rape at a dose of 500-1500 g/Ha, preferably 750-850 g/Ha.

In another embodiment, Napropamide-M may be preferably used in field crops in the range of 450-600 g/Ha.

In another embodiment, Napropamide-M may be used in perennial crops at a dosage of 2000-3000 g/Ha.

In an embodiment, the dicotyledonous weeds especially susceptible to D-Napropamide may be selected from the group consisting of *Acalypha gracilens, Acalypha ostryifolia, Acalypha rhomboidea, Acalypha virginica, Acer rubrum, Acer saccharinum, Actaea pachypoda, Actaea racemosa, Aeschynomene virginica, Agalinis purpurea, Agalinis setacea, Agalinis tenuifolia, Agastache nepetoides, Agastache scrophulariifolia, Ageratina altissima, Ageratina aromatica, Agrimonia parviflora, Agrimonia pubescens, Agrimonia rostellata, Alnus serrulata, Amaranthus cannabinus, Amaranthus hybridus, Amaranthus spinosus, Ambrosia artemisiifolia, Ambrosia trifida, Amelanchier arborea, Amelanchier Canadensis, Amelanchier laevis, Amelanchier obovalis, Amelanchier stolonifera, Amorpha fruticosa, Amphicarpaea bracteata, Anaphalis margaritacea, Anemone quinquefolia, Anemone virginiana, Angelica venenosa, Antennaria plantaginifolia, Apocynum androsaemifolium, Apocynum cannabinum, Aquilegia Canadensis, Arabis lyrata, Aralia nudicaulis, Aralia racemosa, Aralia spinosa, Argemone Mexicana, Aristolochia serpentaria, Arnoglossum atriplicifolium, Arnoglossum reniforme, Artemisia campestris, Artemisia ludoviciana, Asarum canadense, Asclepias amplexicaulis, Asclepias incarnate, Asclepias purpurascens, Asclepias quadrifolia, Asclepias rubra, Asclepias syriaca, Asclepias tuberose, Asclepias variegate, Asclepias verticillata, Aureolaria pedicularia, Aureolaria virginica, Baccharis halimifolia, Baptisia tinctoria, Bartonia paniculata, Bartonia virginica, Betula nigra, Betula populifolia, Bidens aristosa, Bidens bidentoides, Bidens bipinnata, Bidens cernua, Bidens coronate, Bidens discoidea, Bidens frondosa, Bidens laevis, Bidens tripartite, Boehmeria cylindrical, Brasenia schreberi, Brickellia eupatorioides, Cakile edentula, Callitriche heterophylla, Callitriche terrestris, Caltha palustris, Calystegia spithamaea, Campanula aparinoides, Campsis radicans, Cardamine bulbosa, Cardamine concatenate, Cardamine parviflora, Cardamine pensylvanica, Carya alba, Carya glabra, Carya ovate, Carya pallid, Castanea dentate, Castanea pumila, Castilleja coccinea, Catalpa bignonioides, Ceanothus americanus, Celastrus scandens, Celtis occidentalis, Celtis tenuifolia, Cephalanthus occidentalis, Cerastium nutans, Ceratophyllum demersum, Cercis Canadensis, Chaerophyllum procumbens, Chamaecrista fasciculate, Chamaecrista nictitans, Chamaedaphne calyculata, Chamaesyce maculate, Chamaesyce nutans, Chamaesyce polygonifolia, Chamerion angustifolium, Chelone glabra, Chenopodium pratericola, Chenopodium rubrum, Chenopodium simplex, Chimaphila maculate, Chimaphila umbellate, Chionanthus virginicus, Chrysopsis mariana, Chrysosplenium americanum, Cicuta bulbifera, Cicuta maculate, Hybanthus concolor, Hydrastis Canadensis, Hydrocotyle Americana, Hydrocotyle umbellate, Hydrocotyle verticillata, Hypericum boreale, Hypericum canadense, Hypericum crux-andreae, Hypericum densiflorum, Hypericum denticulatum, Hypericum ellipticum, Hypericum gentianoides, Hypericum hypericoides, Hypericum majus, Hypericum mutilum, Hypericum punctatum, Ilex glabra, Ilex laevigata, Ilex mucronata, Ilex opaca, Ilex verticillata, Impatiens capensis, Ionactis linariifolius, Ipomoea pandurata, Itea virginica, Juglans cinerea, Juglans nigra, Kalmia angustifolia, Kalmia* latifolia, Kosteletzkya virginica, Krigia biflora, Krigia virginica, Lactuca biennis, Lactuca Canadensis, Lactuca hirsute, Laportea Canadensis, Lathyrus palustris, Lathyrus venosus, Lechea minor, Lechea mucronata, Lechea racemulosa, Leiophyllum buxifolium, Lepidium densiflorum, Lepidium virginicum, Lespedeza angustifolia, Lespedeza capitata, Lespedeza frutescens, Lespedeza hirta, Lespedeza repens, Lespedeza stuevei, Lespedeza violacea, Lespedeza virginica, Liatris pilosa, Liatris spicata, Limosella australis, Lindera benzoin, Lindernia dubia, Linum intercursum, Linum striatum, Linum virginianum, Liquidambar styraciflua, Liriodendron tulipifera, Lobelia canbyi, Lobelia cardinalis, Lobelia inflate, Lobelia nuttallii, Lobelia spicata, Ludwigia alternifolia, Ludwigia hirtella, Ludwigia palustris, Ludwigia sphaerocarpa, Lupinus perennis, Lycopus americanus, Lycopus amplectens, Lycopus rubellus, Lycopus uniflorus, Lycopus virginicus, Lyonia ligustrina, Lyonia mariana, Lysimachia ciliate, Lysimachia hybrid, Lysimachia quadrifolia, Lysimachia terrestris, Lysimachia thyrsiflora, Magnolia tripetala, Magnolia virginiana, Melampyrum lineare, Menispermum canadense, Mentha-piperita, Mentha arvensis, Menyanthes trifoliate, Micranthemum micranthemoides, Mikania scandens, Mimulus alatus, Mimulus ringens, Minuartia caroliniana, Mirabilis nyctaginea, Mitchella repens, Moehringia lateriflora, Mollugo verticillata, Monarda punctata, Monotropa hypopithys, Monotropa uniflora, Morella caroliniensis, Morella cerifera, Morella pensylvanica, Morus rubra, Myosotis laxa, Myosotis verna, Myrica gale, Myriophyllum humile, Myriophyllum pinnatum, Myriophyllum tenellum, Nelumbo lutea, Nuphar lutea, Nuttallanthus Canadensis, Nymphaea odorata, Nyssa sylvatica, Obolaria virginica, Oclemena nemoralis, Oenothera biennis, Oenothera fruticosa, Oenothera laciniata, Oenothera perennis, Oldenlandia unWora, Oligoneuron rigidum, Onosmodium virginianum, Opuntia humifusa, Orthilia secunda, Osmorhiza claytona, Osmorhiza longistylis, Oxalis dillenii, Oxalis stricta, Oxypolis rigidior, Packera aurea, Packera obovata, Packera paupercula, Panax trifolius, Paronychia Canadensis, Paronychia fastigiata, Parthenocissus quinquefolia, Pedicularis Canadensis, Pedicularis lanceolata, Penstemon hirsutus, Penstemon laevigatus, Penthorum sedoides, Phlox divaricata, Phlox maculate, Phlox pilosa, Phlox subulata, Phoradendron leucarpum, Photinia floribunda, Photinia melanocarpa, Photinia pyrifolia, Phryma leptostachya, Physalis heterophylla, Physalis longifolia, Physalis pubescens, Physocarpus opulifolius, Phytolacca Americana, Pilea Fontana, Pilea pumila, Plantago aristata, Plantago pusilla, Plantago virginica, Platanus occidentalis, Pluchea foetida, Podophyllum peltatum, Polemonium reptans, Polygala brevifolia, Polygala cruciata, Polygala incarnate, Polygala lutea, Polygala mariana, Polygala nuttallii, Polygala polygama, Polygala sanguine, Polygala senega, Polygala verticillata, Polygonella articulate, Polygonum amphibium, Polygonum arifolium, Polygonum careyi, Polygonum erectum, Polygonum hydropiperoides, Polygonum lapathifolium, Polygonum pensylvanicum, Polygonum punctatum, Polygonum robustius, Polygonum sagittatum, Polygonum tenue, Populus grandidentata, Populus tremuloides, Potentilla arguta, Potentilla Canadensis, Potentilla norvegica, Potentilla simplex, Prenanthes altissima, Prenanthes autumnalis, Prenanthes serpentaria, Prenanthes trifoliolata, Proserpinaca intermedia, Proserpinaca palustris, Proserpinaca pectinata, Prunella vulgaris, Prunus Americana, Prunus angustifolia, Prunus maritime, Prunus pumila, Prunus serotina, Pseudognaphalium helleri, Pseudognaphalium obtusifolium, Ptilimnium capillaceum, Pycnanthemum clinopodioides, Pycnanthemum incanum, Pycnanthemum muticum, Pycnanthemum tenuifolium, Pycnanthemum verticillatum, Pycnanthemum virginianum, Pyrola Americana, Pyrola chlorantha, Pyrola elliptica, Pyxidanthera barbulata, Quercus alba, Quercus coccinea, Polygonum pensylvanicum, Polygonum punctatum, Polygonum robustius, Polygonum sagittatum, Polygonum tenue, Populus grandidentata, Populus tremuloides, Potentilla arguta, Potentilla Canadensis, Potentilla norvegica, Potentilla simplex, Prenanthes altissima, Prenanthes autumnalis, Prenanthes serpentaria, Prenanthes trifoliolata, Proserpinaca intermedia, Proserpinaca palustris, Proserpinaca pectinata, Prunella vulgaris, Prunus Americana, Prunus angustifolia, Prunus maritime, Prunus pumila, Prunus serotina, Pseudognaphalium helleri, Pseudognaphalium obtusifolium, Ptilimnium capillaceum, Pycnanthemum clinopodioides, Pycnanthemum incanum, Pycnanthemum muticum, Pycnanthemum tenuifolium, Pycnanthemum verticillatum, Pycnanthemum virginianum, Pyrola Americana, Pyrola chlorantha, Pyrola elliptica, Pyxidanthera barbulata, Quercus alba, Quercus coccinea, Quercus ilicifolia, Quercus marilandica, Quercus michauxii, Quercus palustris, Quercus phellos, Quercus prinoides, Quercus prinus, Quercus rubra, Quercus stellata, Ranunculus ambigens, Ranunculus hispidus, Ranunculus longirostris, Ranunculus pensylvanicus, Ranunculus pusillus, Ranunculus recurvatus, Ranunculus sceleratus, Ranunculus trichophyllus, Rhexia mariana, Rhexia virginica, Rhododendron maximum, Rhododendron periclymenoides, Rhododendron prinophyllum, Rhododendron viscosum, Rhus copallinum, Rhus glabra, Rhus typhina, Ribes americanum, Robinia pseudoacacia, Robinia viscose, Rorippa palustris, Rosa Carolina, Rotala ramosior, Rubus Canadensis, Rubus cuneifolius, Rubus flagellaris, Rubus hispidus, Rubus occidentalis, Rudbeckia hirta, Rudbeckia laciniata, Rumex altissimus, Rumex orbiculatus, Sabatia angularis, Sabatia difformis, Sagina decumbens, Salix bebbiana, Salix discolor, Salix eriocephala, Salix humilis, Salix interior, Salix nigra, Salix petiolaris, Salix sericea, Salvia lyrata, Sanguinaria Canadensis, Sanguisorba Canadensis, Sanicula Canadensis, Sanicula marilandica, Sarracenia purpurea, Saururus cernuus, Saxifraga pensylvanica, Saxifraga virginiensis, Schwalbea Americana, Scrophularia lanceolata, Scrophularia marilandica, Scutellaria elliptica, Scutellaria galericulata, Scutellaria integrifolia, Scutellaria lateriflora, Senna hebecarpa, Sericocarpus asteroids, Sericocarpus linifolius, Sicyos angulatus, Sida spinosa, Silene antirrhina, Silene stellata, Sium suave, Solanum carolinense, Solanum ptycanthum, Solanum rostratum, Solidago bicolor, Solidago caesia, Solidago erecta, Solidago fistulosa, Solidago flexicaulis, Solidago gigantean, Solidago juncea, Solidago latissimifolia, Solidago nemoralis, Solidago odora, Solidago patula, Solidago puberula, Solidago rugosa, Solidago sempervirens, Solidago stricta, Solidago uliginosa, Solidago ulmifolia, Spergularia salina, Spiraea alba, Stachys hyssopifolia, Stachys palustris, Stachys tenuifolia, Staphylea trifolia, longifolia, Stellaria pubera, Strophostyles helvola, Strophostyles umbellate, Stylosanthes biflora, Symphyotrichum cordifolium, Symphyotrichum dumosum, Symphyotrichum ericoides, Symphyotrichum leave, Symphyotrichum lanceolatum, Symphyotrichum lateriflorum, Symphyotrichum novi-belgii, Symphyotrichum patens, Symphyotrichum pilosum, Symphyotrichum puniceum, Symphyotrichum subulatum, Symphyotrichum undulatum, Teucrium canadense, Thalictrum pubescens, Thalictrum revolutum, Thalictrum thalictroides, Thaspium barbinode, Thaspium trifoliatum, Tilia Americana, Toxicodendron pubescens, Toxicodendron radicans, Toxicoden-

*dron vernix, Triadenum virginicum, Trichosterna brachiatum, Trichosterna dichotomum, Trichosterna setaceum, Trientalis borealis, Triodanis perfoliata, Ulmus Americana, Ulmus rubra, Utricularia geminiscapa, Utricularia gibba, Utricularia intermedia, Utricularia juncea, Utricularia macrorhiza, Utricularia purpurea, Utricularia radiate, Utricularia striata, Utricularia subulata, Vaccinium angustifolium, Vaccinium corymbosum, Vaccinium fuscatum, Vaccinium macrocarpon, Vaccinium stamineum, Valerianella umbilicata, Verbena hastate, Verbena simplex, Verbena urticifolia, Verbesina alternifolia, Veronica anagallis-aquatica, Veronica peregrine, Veronica scutellata, Veronicastrum virginicum, Viburnum acerifolium, Viburnum dentatum, Viburnum nudum, Viburnum prunifolium, Violapalmate, Viola affinis, Viola bicolor, Viola blanda, Viola brittoniana, Viola cucullata, Viola hirsutula, Viola labradorica, Viola lanceolata, Viola macloskeyi, Viola pedata, Viola pubescens, Viola sagittata, Viola triloba, Vitis aestivalis, Vitis labrusca, Vitis riparia, Vitis vulpine, Xanthium strumarium*, and *Zizia aptera*.

In another embodiment, the use and method of the present invention is effective against dicotyledonous weeds selected from *Cirsium arvense, Taraxacum officinale, Ranunculus repens, Senecio vulgaris, Papaver rohoeas, Veronica persica, Matricaria* sp., *Fallopia convolvulus, Veronica arvensis, Veronica hederofolia, Stellaria media*, and *Polygonum convolvulus*.

In another embodiment, the present invention provides a herbicidal composition comprising D Napropamide and agronomically acceptable excipients. These compositions were found useful in the practice of the enhanced use and improved method of the present invention. The agronomically acceptable excipients may be selected from carriers, inert materials, organic or inorganic solvents, minerals, mixed solvents, wetting agents and/or emulsifying agents, adhesive agents, anti-caking agents, deflocculating agents, and the like. The herbicidal composition may be formulated in the form of solid and liquid formulations.

In another aspect, the present invention provides a combination comprising Napropamide-M along with a second herbicide selective for monocotyledonous weeds. It was surprisingly found that a broad-spectrum herbicide effect was achieved with a reduced overall amount of active ingredient when Napropamide-M was combined with a second herbicide.

The present invention therefore also provides a herbicide combination which comprises: (a) D-Napropamide; and (b) a second herbicide which is active against monocotyledonous weeds.

In an embodiment, the second herbicide selected is such that not only it is active against monocotyledonous weeds but is, preferably, relatively more active against monocotyledonous weeds than dicotyledonous weeds.

Further, following the finding of the present invention that D-Napropamide has enhanced activity specifically against dicotyledonous weeds, it is possible to formulate the herbicide such that it is active in controlling dicotyledonous weeds, yet is less active (preferably substantially inactive) against monocotyledonous plant species. Accordingly, the present invention also provides the use of D-Napropamide for the control of a dicotyledonous weed at a locus, wherein the D-Napropamide is applied in an amount such that it is effective in controlling said dicotyledonous weed, yet is less active (preferably substantially inactive) against monocotyledonous plant species.

Typically, said monocotyledonous plant species may be a crop plant.

In this embodiment, the activity of the D-Napropamide against the monocotyledonous plant species is typically such that the mean final foliar fresh weight of the monocotyledonous plant species 21 days after application of the D-Napropamide is 70% or more, more typically 80% or more, preferably 90% or more, than the weight obtained with untreated plants.

In an embodiment, the second herbicide is selected from but not limited to, clomazone, a urea herbicide, a triazine herbicide, a hydroxybenzonitrile herbicide, a thiocarbamate herbicide, a pyridazine herbicide, chloroacetanilide herbicides; benzothiazole herbicides; carbanilate herbicides, cyclohexene oxime herbicides; picolinic acid herbicides; pyridine herbicides; quinolinecarboxylic acid herbicides; chlorotriazine herbicides, aryloxyphenoxypropionic herbicides, oxadiazolone herbicides; phenylurea herbicides, sulfonanilide herbicides; triazolopyrimidine herbicides, amide herbicides, pyridazine herbicides, dinitroaniline herbicides, or combinations thereof.

In another preferred embodiment the present invention provides a herbicidal combination which comprises: (a) D-Napropamide; and (b) clomazone.

In another preferred embodiment the present invention provides a herbicidal combination which comprises: (a) D-Napropamide; and (b) Benfluralin.

In yet another embodiment the present invention provides use of combination comprising combination of D-Napropamide and a second herbicide for the control of weeds at a locus.

In another preferred embodiment the present invention provides a method of controlling the weed infestation at a locus by treating with a combination comprising combination of D-Napropamide and a second herbicide.

In another preferred embodiment the present invention provides a herbicidal combination which comprises: (a) D-Napropamide; and (b) Clomazone.

In a preferred embodiment, clomazone is combined with Napropamide-M as an encapsulated capsule suspension. In one embodiment, the capsule suspension formulation of clomazone is as described in U.S. Reissue Pat. No. RE38675, U.S. Pat. No. 5,583,090, U.S. Pat. No. 5,783,520, or PCT Publication No. WO/2011/121407, all of which are incorporated herein by reference.

In another embodiment, the present invention provides a herbicidal combination comprising (a) Napropamide-M; (b) an urea herbicide selected from benzthiazuron, cumyluron, cycluron, dichloralurea, diflufenzopyr, isonoruron, isouron, methabenzthiazuron, monisouron, noruron, anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron, thidiazuron, amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metazosulfuron, methiopyrisulfuron, monosulfuron, nicosulfuron, orthosulfamuron, oxasulfuron, primisulfuron, propyrisulfuron, pyrazosulfuron, rimsulfuron, sulfometuron, sulfosulfuron, trifloxysulfuron, zuomihuanglong, chlorsulfuron, cinosulfuron, ethametsulfuron, iodosulfuron, iofensulfuron, metsulfuron, prosulfiron, thifensulfuron, triasulfuron, tribenuron, triflusulfuron, tritosulfuron, buthiuron, ethidimuron, tebuthiuron, thiazafluron, and thidiazuron; and (c) an agriculturally acceptable carrier or diluent.

In an embodiment, the present invention provides a combination comprising (a) Napropamide-M; and (b) dimefuron.

In an embodiment, Napropamide-M is combined with a triazine herbicide selected from the group consisting of dipropetryn, fucaojing, trihydroxytriazine, atrazine, chlorazine, cyanazine, cyprazine, eglinazine, ipazine, mesoprazine, procyazine, proglinazine, propazine, sebuthylazine, simazine, terbuthylazine, trietazine, indaziflam, triaziflam, atraton, methometon, prometon, secbumeton, simeton, terbumeton, ametryn, aziprotryne, cyanatryn, desmetryn, dimethametryn, methoprotryne, prometryn, simetryn, and terbutryn.

In another embodiment, Napropamide-M may be combined with a nitrile herbicide selected from bromobonil, bromoxynil, chloroxynil, dichlobenil, iodobonil, ioxynil, and pyraclonil.

In an embodiment, Napropamide-M may be combined with a thiocarbamate herbicide selected from dazomet and metam.

In another embodiment, Napropamide-M may be combined with a pyridazine herbicide selected from credazine, cyclopyrimorate, pyridafol, and pyridate.

In another embodiment, Napropamide-M may be combined with a chloroacetanilide herbicide selected from acetochlor, alachlor, butachlor, butenachlor, delachlor, diethatyl, dimethachlor, ethachlor, ethaprochlor, metazachlor, metolachlor, S-metolachlor, pretilachlor, propachlor, propisochlor, prynachlor, terbuchlor, thenylchlor, and xylachlor.

In another embodiment, Napropamide-M may be combined with a benzothiazole herbicide selected from benazolin, benzthiazuron, fenthiaprop, mefenacet, and methabenzthiazuron.

In another embodiment, Napropamide-M may be combined with a carbanilate herbicide selected from a carbanilate herbicide selected from barban, BCPC, carbasulam, carbetamide, CEPC, chlorbufam, chlorpropham, CPPC, desmedipham, phenisopham, phenmedipham, phenmedipham-ethyl, propham, and swep.

In another embodiment, Napropamide-M may be combined with a cyclohexene oxime herbicide selected from alloxydim, butroxydim, clethodim, cloproxydim, cycloxydim, profoxydim, sethoxydim, tepraloxydim, and tralkoxydim.

In another embodiment, Napropamide-M may be combined with a picolinic acid herbicide selected from aminopyralid, clopyralid, halauxifen, and picloram.

In an embodiment, Napropamide-M may be combined with a pyridine herbicide selected from aminopyralid, cliodinate, clopyralid, diflufenican, dithiopyr, flufenican, fluroxypyr, halauxifen, haloxydine, picloram, picolinafen, pyriclor, pyroxsulam, thiazopyr, and triclopyr.

In an embodiment, Napropamide-M may be combined with a quinoline carboxylic acid herbicide selected from quinclorac and quinmerac.

In another embodiment, Napropamide-M may be combined with an aryloxyphenoxypropionic acid herbicide selected from cloprop, 4-CPP, dichlorprop, dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P, and trifop.

In another embodiment, Napropamide-M may be combined with a oxadiazolone herbicide selected from dimefuron, methazole, oxadiargyl, and oxadiazon.

In another embodiment, Napropamide-M may be combined with a sulfoanilide herbicide selected from benzofluor, cloransulam, diclosulam, florasulam, flumetsulam, metosulam, perfluidone, profluazol, and pyrimisulfan.

In another embodiment, Napropamide-M may be combined with a triazolopyrimidine herbicide selected from cloransulam, diclosulam, florasulam, flumetsulam, metosulam, penoxsulam, and pyroxsulam.

In another embodiment, Napropamide-M may be combined with amide herbicides selected from allidochlor, amicarbazone, beflubutamid, benzadox, benzipram, bromobutide, cafenstrole, CDEA, cyprazole, dimethenamid, dimethenamid-P, diphenamid, epronaz, etnipromid, fentrazamide, flucarbazone, flupoxam, fomesafen, halosafen, huangcaoling, isocarbamid, isoxaben, naptalam, pethoxamid, propyzamide, quinonamid, saflufenacil, tebutam, and tiafenacil.

In another embodiment, Napropamide-M may be combined with a pyridazine herbicide selected from credazine, cyclopyrimorate, pyridafol, and pyridate.

In an embodiment, Napropamide-M may be combined with glufosinate. An additional advantage demonstrated by this combination was that Napropamide-M acted pre-emergence while any weeds emerged was quickly killed by the glufosinate component thereby rendering the pre-emergent herbicide Napropamide-M active yet again. Therefore, the combination of Napropamide-M with glufosinate was found to be surprisingly efficacious as a pre-emergent and broad spectrum post-emergent herbicide.

In yet another embodiment, Napropamide-M may be combined with a dinitroaniline herbicide selected from benfluralin, butralin, chlornidine, dinitramine, dipropalin, ethalfluralin, fluchloralin, isopropalin, methalpropalin, nitralin, oryzalin, pendimethalin, prodiamine, profluralin, and trifluralin.

In another embodiment, Napropamide-M may be combined with a third herbicide. The third herbicide may be selected from the herbicides listed above in any of the embodiments although the second and third herbicides may not be the same.

In yet another preferred embodiment the present invention further comprises third herbicide selected from clomazone, chloroacetanilide herbicides; pyrazole herbicides; quinolinecarboxylic acid herbicides; and amide herbicides.

In this embodiment, the chloroacetanilide herbicide, pyrazole herbicides, quinoline carboxylic acid herbicide and amide herbicide may be selected from the list of compounds defined in the embodiments described above for these classes of compounds.

In another embodiment the present invention also provides a herbicide combination which comprises: (a) D-Napropamide; (b) a second herbicide; and (c) a third herbicide.

In yet another embodiment the present invention provides a ternary herbicidal combination which comprises D-Napropamide; benfluralin; and clomazone.

In yet another embodiment the present invention provides a ternary herbicidal combination which comprises D-Napropamide; dimethachlor; and clomazone.

In another embodiment, the present invention provides a combination comprising:
(a) Napropamide-M; and (b) a second herbicide component
  selected from any one of:
  (i) S-Metolachlor;
  (ii) Clomazone;

(iii) Flufenacet;
(iv) Diflufenican;
(v) Flufenacet+diflufenacet;
(vi) Benfluraline;
(vii) Quinmerac;
(viii) Metazachlor;
(ix) Quinmerac+Metazachlor;
(x) Glufosinate;
(xi) Metribuzin;
(xii) Clomazone+S-Metolachlor;
(xiii) Dimethachlor;
(xiv) Benazolin;
(xv) Carbetamide;
(xvi) Clethodim;
(xvii) Cycloxydim;
(xviii) Sethoxydim;
(xix) Clopyralid;
(xx) Cyanazine;
(xxi) Simazine;
(xxii) Diclofop;
(xxiii) Fenoxaprop-P;
(xxiv) Fluazifop-P;
(xxv) Haloxyfop-P;
(xxvi) Propaquizafop;
(xxvii) Quizalafop;
(xxviii) Dimefuron;
(xxix) Flumetsulam;
(xxx) Propyzamide;
(xxxi) Pyridate;
(xxxii) Trifluralin; and
(xxxiii) Clomazone+Metazachlor.

The compound Napropamide-M is known in the art and can be prepared by any of the known methods such as the one disclosed in WO2009004642, which is incorporated herein by reference in its entirety.

The invention will now be explained in more detail in the following examples that illustrate, but are not intended to limit, the invention.

EXAMPLES

Field trials were conducted on various moncotyledonous weeds and dicotyledonous weeds and the effect of D-isomer of Napropamide was studied to understand the selective and effective control of dicotyledonous weeds over monocotyledonous weeds. The effect of D-isomer of Napropamide in comparison to racemic napropamide and untreated was studied, which is concluded herein below:

Statistical Analysis Model:

Several small plot replicated trials were carried out to evaluate and/or compare the efficacy of D-Napropamide against a range of indicated annual broadleaved and grass weed species in the indicated crops. No problems were encountered during mixing or application of any of the product formulations or tank mixtures under test.

In each of the reported data, the homogeneity of variance was tested by Bartlett's test. Wherever this test indicated no homogeneity of variance, the transformed values were used for analysis of variance. Assessment data was then analyzed using a two-way analysis of variance (ANOVA) on untransformed and transformed data. The probability of no significant differences occurring between treatment means was calculated as the F probability value (p(F)). A mean comparison test was only performed and reported when the treatment of F that was calculated during analysis of variance was significant at the observed significance level specified for the mean comparison test. Where the data was transformed, treatment means in the reports were presented in their detransformed state, with the appropriate letter test and mean descriptions (LSD and standard deviation) derived from the transformed ANOVA.

Example 1

Controlled Trial: Comparative Effect of D-Isomer of Napropamide and Napropamide for Controlling *Stellaria media* (Dicot Weed) and *Poa annua* (Monocot Weed)

A study was carried out to determine the relative biological activity of the D and L isomers of Napropamide when applied pre-emergence to one monocotyledon and one dicotyledon species. Napropamide, containing 450 grammes active substance per litre (g a.s./L) formulated as a suspension concentrate and the D-isomer of Napropamide (1000 g a.s./L) were applied at a range of concentrations from 0.1575 to 1.26 kilograms of active substance per hectare (kg a.s/Ha).

$EC_{50}$ values in kg a.s./Ha were calculated from the dose response data using final foliar fresh weight data for each species and was used to determine the relative biological activity of the D and L isomers of Napropamide. The methodology was based on the OECD guideline 2008, according to the revision of July 2006 for seedling emergence and growth. The study was conducted to GLP standards.

Seeds were sown directly into non-porous plastic pots containing the following mix of soil: 10 L of sterile loam+4 L of coarse grit (washed quartztite, nominal 4 mm)+10 L of sand. This soil mix was characterized as a sandy loam with an organic carbon content of 1.5% and pH of 7.2. Details of the plant species, number of seeds per pot and pot size are shown below. All seeds were sown 1-2 cm deep.

TABLE 1

| Details of Plant Species | | | | | |
|---|---|---|---|---|---|
| Weed type | Species | Common name | Variety(Source) | Seeds/pot | Pot size |
| Monocotyledon | *Poa annua* | Meadow grass | Herbiseed | 4 | 7 × 7 × 8 cm |
| Dicotyledon | *Stellaria media* | Chickweed | Herbiseed | 6 | 7 × 7 × 8 cm |

The highest concentration of Napropamide was prepared by measuring a calculated volume by weight and diluting with tap water to the full required volume. Lower concentrations were prepared by serial dilution with water. D-Napropamide was prepared by dissolving the calculated weight in acetone and adding water to give the full required volume in 50:50 acetone+water. Lower concentrations were prepared by serial dilution with 50:50 acetone+water. D-Napropamide dissolved completely.

TABLE 2

Preparation of the Highest Rate Spray Solutions for *Poa annua*

| Test item | Active Ingredient | Rate | Application volume | Amount weighed | Volume prepared |
|---|---|---|---|---|---|
| Napropamide | 450 g as/L | 1.26 kg as/L | 193.12 L/Ha | 6.321 g | 400 mL (water) |
| D-Napropamide | 1000 g as kg | 1.26 kg as/L | 193.12 L/Ha | 2.611 g | 400 mL (acetone + water) |

TABLE 3

Preparation of Highest Rate Spray Solutions for *Stellaria media*

| Test item | Active Ingredient | Rate | Application volume | Amount weighed | Volume prepared |
|---|---|---|---|---|---|
| Napropamide | 450 g as/L | 1.26 kg as/L | 196.17 L/Ha | 6.223 g | 400 mL (water) |
| D-Napropamide | 1000 g as kg | 1.26 kg as/L | 196.17 L/Ha | 2.569 g | 400 mL (acetone + water) |

The sprayer was calibrated within 24 hours prior to application by weight of 15 applications of water to six 86 mm ID petri dishes. The total weight of water over a known area enabled a simple calculation giving the volume rate to be made. The volume rate achieved was within the range specified in the study plan (200 L/Ha±10%).

Replication was five pots per treatment for each plant species. After application, pots were placed on the bench in glasshouse in randomized blocks. Plants were assessed for emergence, mortality and visual injury (expressed as a percentage of the untreated control: 0%=no injury, 1-39%=slight injury, 40-69%=moderate injury, 70-99%=severe injury and 100%-=all plants dead) at 14 and 21 days after 50% emergence in the untreated controls. Fresh weights (biomass above soil level) were also recorded 21 days after 50% emergence in the untreated controls. Plants were fully turgid at the time of harvest.

TABLE 4

Mean Final Foliar Fresh Weights (g)

| Treatment | Rate (kg/Ha) | Poa annua | Stellaria media |
|---|---|---|---|
| Untreated | Acetone + Water | 0.90 | 1.44 |
| D-Napropamide | 0.1575 | 0.93 | 0.498 |
| D-Napropamide | 0.315 | 0.64 | 0.198 |
| D-Napropamide | 0.63 | 0.45 | 0.17 |
| Napropamide | 0.315 | 0.57 | 0.3 |
| Napropamide | 0.63 | 0.98 | 0.328 |

D-Napropamide demonstrates distribution of enhanced activity towards control of dicot weed vis-à-vis only a moderate selectivity towards monocot weed in comparison with Napropamide.

TABLE 5

Mean Final Foliar Fresh Weights Expressed as Percentage of Untreated Controls

| Treatment | Rate (kg/Ha) | Poa annua | Stellaria media |
|---|---|---|---|
| Untreated | Acetone + Water | 100 | 100 |
| D-Napropamide | 0.1575 | 100 | 35 |
| D-Napropamide | 0.315 | 71 | 14 |
| D-Napropamide | 0.630 | 50 | 12 |
| Napropamide | 0.1575 | 100 | 70 |
| Napropamide | 1.26 | 23 | 16 |

D-Napropamide demonstrates distribution of enhanced activity towards control of dicot weed vis-à-vis only a moderate selectivity towards monocot weed in comparison with Napropamide.

Assessment data was recorded on pro-forma sheets and entered into Gylling ARM 7 software. $EC_{50}$ values were calculated using audited means data from the final assessments (21 day). Gylling ARM 7.0 software used a simple probit-maximum likelihood estimation method with 99% confidence level. The $EC_{50}$ values generated were then visually checked against the means data table to verify they appeared correct.

TABLE 6

$EC_{50}$ Values in Kg as/Ha Based on the Final Fresh Weights

| Type of weed | Species | Common name | | $EC_{50}$ (kg/Ha) |
|---|---|---|---|---|
| Monocot | Poa annua | Meadow grass | d-Napropamide | 0.44 |
| | | | l-Napropamide | 1.26 |
| | | | Napropamide | 0.72 |
| Dicot | Stellaria media | Chickweed | d-Napropamide | 0.054 |
| | | | L-Napropamide . . . | 1.26 |
| | | | Napropamide | 0.22 |

Conclusion: D-Napropamide demonstrates distribution of enhanced activity towards control of dicot weed vis-a-vis only a moderate selectivity towards monocot weed in comparison with Napropamide. D-Napropamide was found about 1.63 times more active than racemic Napropamide and 2.86 more active than L-Napropamide in monocotyledonous weeds. Surprisingly, D-Napropamide was found to be about 4.07 times more active than racemic Napropamide and 23.33 times more active than L-Napropamide in dicotyledonous weeds. The degree of enhancement in efficacy seen over racemic Napropamide and L-Napropamide towards the control of dicotyledonous weeds was surprising. Equally surprising was a clear trend of differentiated selectivity of D-Napropamide towards the control of dicotyledonous weeds vis-a-vis the control of monocotyledonous weeds.

Example 2

Selectivity of D-Napropamide for Controlling *Ranunculus repens, Senecio Vulgaris*, and *Papaver rhoeas* (Dicotyledonous Weed) in Strawberry Farm Trial was carried out on strawberries to evaluate the efficacy and selectivity of D-Napropamide and equivalent rate of DEVRINOL® (napropamide) applied pre-emergence. Efficacy was assessed visually after the emergence of significantly new growth in untreated plot. The percentage control of D-isomer of Napropamide and DEVRINOL® was assessed in comparison to the untreated after 224 days after application.

TABLE 7

Mean Percentage Control of *Ranunculus repens* (dicotyledonous weed)

| S No. | Treatment | Percentage Control at 224 DAA | Treatment | Percentage Control at 224 DAA |
|---|---|---|---|---|
| 1 | Untreated | 0.00 | | |
| 2 | Napropamide 5 L/Ha | 33.3 | D-Napropamide 3.0 L/Ha | 66.7 |
| 3 | Napropamide 7 L/Ha | 66.7 | D-Napropamide 4.2 L/Ha | 100 |
| 4 | Napropamide 14 L/Ha | 83.3 | D-Napropamide 8.5 L/Ha | 100 |

LSD (P = 0.5): 4.640;
SD: 3.179

The tested formulations contained 450 g/L of Napropamide and Napropamide-M, respectively.

Conclusion: D-Napropamide demonstrated surprising efficacy in the control of *Ranunculus repens* vis-à-vis the control achieved by Napropamide at an equivalent dosage.

TABLE 8

Mean Percentage Control of *Senecio vulgaris*

| S No. | Treatment | Percentage Control at 70 DAA | Treatment | Percentage Control at 70 DAA |
|---|---|---|---|---|
| 1 | Untreated | 0.00 | | |
| 2 | Napropamide 5 L/Ha | 37.5 | D-Napropamide 3.0 L/Ha | 75.0 |
| 3 | Napropamide 7 L/Ha | 25.0 | D-Napropamide 4.2 L/Ha | 50.0 |
| 4 | Napropamide 14 L/Ha | 12.5 | D-Napropamide 8.5 L/Ha | 75.0 |

The tested formulations contained 450 g/L of Napropamide and Napropamide-M, respectively.

Conclusion: D-Napropamide demonstrated surprising efficacy in the control of *Senecio vulgaris*, a dicotyledonous weed, vis-à-vis the control achieved by Napropamide at an equivalent dosage.

TABLE 9

Mean Percentage Control of *Papaver rhoeas*

| S No. | Treatment | Percentage Control at 70 DAA | Treatment | Percentage Control at 70 DAA |
|---|---|---|---|---|
| 1 | Untreated | 0.00 | | |
| 2 | Napropamide 5 L/Ha | 62.5 | D-Napropamide 3.0 L/Ha | 71.7 |
| 3 | Napropamide 7 L/Ha | 81.7 | D-Napropamide 4.2 L/Ha | 95.0 |
| 4 | Napropamide 14 L/Ha | 82.5 | D-Napropamide 8.5 L/Ha | 95.7 |

The tested formulations contained 450 g/L of Napropamide and Napropamide-M, respectively.

Conclusion: D-Napropamide demonstrated surprising efficacy in the control of *Papaver rhoeas* vis-à-vis the control achieved by Napropamide at an equivalent dosage.

Example 3

Selectivity of D-Isomer of Napropamide for Controlling Annual Broadleaved and Grass Weed Species in Winter Oilseed Rape Trials were conducted to evaluate the selectivity and efficacy of D-isomer of Napropamide when applied pre-emergence to oilseed rape crop. The % control of weed was assessed at regular intervals.

TABLE 10

Mean Percentage Control of *Apera spica-venti* (Monocot Weed)

| S No. | Treatment | Percentage Control at 63 DAA | Treatment | Percentage Control at 63 DAA |
|---|---|---|---|---|
| 1 | Untreated | 0.00 | | |
| 2 | D-Napropamide 1.4 L/Ha | 35.00 | Napropamide 1.6 L/Ha | 40.00 |
| 3 | D-Napropamide 1.6 L/Ha | 52.50 | Napropamide 2.8 L/Ha | 76.25 |
| 4 | D-Napropamide 1.6 L/Ha | 58.75 | Napropamide 2.8 L/Ha | 67.50 |

LSD (P = 0.5): 10.367

The tested formulations contained 450 g/L of Napropamide and Napropamide-M, respectively.

Conclusion: D-Napropamide demonstrates poor efficacy in the control of *Apera spica-venti*, a monocot weed, vis-à-vis the control achieved by Napropamide at an equivalent dosage.

TABLE 11

Mean Percentage Control of *Veronica persica* (Dicot Weed)

| S No. | Treatment | Percentage Control at 63 DAA | Treatment | Percentage Control at 63 DAA |
|---|---|---|---|---|
| 1 | Untreated | 0.00 | | |
| 2 | D-Napropamide 1.4 L/Ha | 100.00 | Napropamide 1.6 L/Ha | 75.00 |
| 3 | D-Napropamide 1.6 L/Ha | 100.00 | Napropamide 2.8 L/Ha | 75.00 |

LSD (P = 0.5): 10.367

The tested formulations contained 450 g/L of Napropamide and Napropamide-M respectively.

Conclusion: D-Napropamide demonstrates superior efficacy in the control of *Veronica persica*, a dicot weed, vis-à-vis the control achieved by Napropamide at an equivalent dosage.

TABLE 12

Mean Percentage Control of *Triticum aestivum* (Monocot Weed)

| S No. | Treatment | Percentage Control at 51 DAA | Treatment | Percentage Control at 72 DAA |
|---|---|---|---|---|
| 1 | Untreated | 0.00 | | |
| 2 | D-Napropamide 450 g/L @ 1.4 L/Ha | 0.00 | D-Napropamide 450 g/L @ 1.4 L/Ha | 0.00 |
| 3 | D-Napropamide 450 g/L @ 1.6 L/Ha | 0.00 | D-Napropamide 450 g/L @ 1.6 L/Ha | 0.00 |
| 4 | D-Napropamide 450 g/L @ 1.8 L/Ha | 0.00 | D-Napropamide 450 g/L @ 1.8 L/Ha | 0.00 |
| 5 | D-Napropamide 450 g/L @ 2.0 L/Ha | 0.00 | D-Napropamide 450 g/L @ 2.0 L/Ha | 0.00 |

LSD (P = 0.5): 0.000;
SD: 0.000

Conclusion: D-Napropamide demonstrates negligible control of *Triticum aestivum*, a monocot weed.

TABLE 13

Mean Percentage Control of *Cirsium arvense* (Dicot Weed)

| S No. | Treatment | Percentage Control at 51 DAA | Treatment | Percentage Control at 51 DAA |
|---|---|---|---|---|
| 1 | Untreated | 0.00 | | |
| 2 | D-Napropamide 450 g/L @ 1.6 L/Ha | 100.00 | Napropamide 450 g/L @ 1.6 L/Ha | 20.00 |

Conclusion: D-Napropamide demonstrates superior control of *Cirsium arvense*, a dicot weed vis-à-vis a negligible control of the same weed with an equivalent dosage of Napropamide.

TABLE 14

Mean Percentage Control of *Senecio vulgaris*

| S No. | Treatment | Percentage Control at 214 DAA | Treatment | Percentage Control at 63 DAA |
|---|---|---|---|---|
| 1 | Untreated | 0.00 | | |
| 2 | D-Napropamide 450 g/L @ 1.6 L/Ha | 94.72 | Napropamide 450 g/L @ 1.6 L/Ha | 36.96 |
| 3 | D-Napropamide 450 g/L @ 1.6 L/Ha | 82.15 | Napropamide 450 g/L @ 2.8 L/Ha | 4.65 |

LSD (P = 0.5): 24.514;
SD: 16.862

Conclusion: D-Napropamide demonstrates superior efficacy in the control of *Senecio vulgaris*, a dicot weed, vis-à-vis the control achieved by Napropamide at an equivalent dosage.

TABLE 15

Mean Percentage Control of *Matricaria* sp.

| S No. | Treatment | Percentage Control at 49 DAA | Treatment | Percentage ground cover % |
|---|---|---|---|---|
| 1 | Untreated | 0.00 | Untreated | 4.50 (0.0%) |
| 2 | D-Napropamide 450 g/L @ 2.0 L/Ha | 97.00 | Napropamide 450 g/L @ 1.6 L/Ha | 0.30 (99.3%) |
| 3 | D-Napropamide 450 g/L @ 1.6 L/Ha | 82.15 | Napropamide 450 g/L @ 2.8 L/Ha | 2.13 (52.8%) |

LSD (P = 0.5): 24.514; SD: 16.862
LSD: 1.189; SD: 0.818

Conclusion: D-Napropamide demonstrates superior efficacy in the control of *Matricaria* sp., a dicot weed, vis-à-vis the control achieved by Napropamide at an equivalent dosage.

TABLE 16

Mean Percentage Control of *Fallopia convolvulus* (Dicot Weed)

| S No. | Treatment | Percentage Control at 63 DAA | Treatment | Percentage Control at 63 DAA |
|---|---|---|---|---|
| 1 | Untreated | 0.00 | Untreated | 0.00 |
| 2 | D-Napropamide 450 g/L @ 2.0 L/Ha | 100.00 | Napropamide 450 g/L @ 1.6 L/Ha | 30.00 |
| 3 | D-Napropamide 450 g/L @ 1.6 L/Ha | 100.00 | Napropamide 450 g/L @ 2.8 L/Ha | 0.00 |

Conclusion: D-Napropamide demonstrates superior efficacy in the control of *Fallopia convolvulus*, a dicot weed, vis-à-vis the control achieved by Napropamide at an equivalent dosage.

Example 4

Effect of D-Isomer of Napropamide for Controlling *Digitaria sanguinalis* (Monocot Weed)

A plot with 20% density of *Digitaria sanguinalis* (monocot weed) was treated with D-Napropamide and Racemic Napropamide formulations containing 450 g/L active ingredient and the activity was noted after 60 days of application.

TABLE 17

Mean Percentage Control of *Digitaria sanguinalis*

| S. No. | Treatment | % Control 16 DAA | % Control 33 DAA |
|---|---|---|---|
| | Treatment evaluation interval | 16 DAA | 33 DAA |
| | BBCH Weed | 12 | 21 |
| | Groundcover (%) weed | 4.75 | 7.0 |
| 1 | D-Napropamide 3 L/Ha | 7.50 | 8.75 |
| 2 | D-Napropamide 4.5 L/Ha | 10.00 | 10.00 |
| 3 | D-Napropamide 6 L/Ha | 10.00 | 12.50 |
| 4 | D-Napropamide 7.5 L/Ha | 10.00 | 11.25 |
| 5 | D-Napropamide 9 L/Ha | 10.00 | 18.75 |
| 6 | Napropamide 9 L/Ha | 12.50 | 15.00 |
| LSD (P = 0.05) | | 4.675 | 4.682 |
| Std. Dev. | | 3.162 | 3.107 |
| CV | | 31.62 | 24.45 |

Conclusion: D-Napropamide is only as efficacious or less in comparison to Napropamide in the control of monocotyledonous weeds.

Example 5

Broad Spectrum Effect of D-Napropramid and Clomazone on Dicot and Monocot Weeds The effect of combination of D-napropramide and Clomazone was tested in the field, post sowing of the seeds. The combination of D-napropramide and Clomazone was tested at different amounts on monocot and dicot weeds. The field was observed after 50 days, results of which are reproduced herein below:

TABLE 18

Percentage Control

|  |  | D-Napropamide (450 g/L SC @ 1.7 l) + Clomazone (360 g/L CS @ 0.25 l) (% control) | D-Napropamide (91 g/L MEC @ 8.41 l) + Clomazone (360 g/L CS @ 0.25 l) (% control) |
|---|---|---|---|
| ALOMY (19/m²) | *Alopecurus myosuroides* Huds (monocot) | 100 | 100 |
| LOLMU (192/m²) | *Lolium multiflorum* Lam (monocot) | 100 | 100 |
| PAPRH (15/m²) | *Papaver rhoeas* L. | 100 | 100 |
| CENCY (104/m²) | *Centaurea cyanus* L. (dicot) | 100 | 100 |
| GERPU (156/m²) | *Geranium pusillum* L. (dicot) | 100 | 100 |
| GERDI (148/m²) | *Geranium dissectum* L (dicot) | 100 | 98.3 |
| TRZAW (88/m²) | Wheat (monocot) | 100 | 98.3 |
| HORVW (89/m²) | *Hordeum irregulare* Aberg & Wiebe (monocot) | 100 | 100 |
| BARVU (78/m²) | *Barbarea vulgaris* Ait. f. (dicot) | 100 | 100 |

It was concluded that the combination of D-Napropamide and Clomazone was very effective in controlling both the dicot weeds and monocot weeds.

Example 6

Broad Spectrum Effect of D-Napropramid and Combination of Dimetachlor+Clomazone The field infected with TRZAW (wheat-monocot) 20/m² was treated with D-napropramid (1.2 L/ha) and in combination with dimethachlor+Clomazone (1.5 L/ha). The result is tabulated herein below:

TABLE 19

|  | Column 1 |
|---|---|
| D-Napropamide (450 g/L SC @ 1.2 l) + dimethachlor + Clomazone (500 g/L dimethachlor + 360 g/L clomazone @ 1.5 l) | 93 |
| D-Napropamide (450 g/L SC @ 1.2 l) + dimethachlor + Clomazone (500 g/L dimethachlor + 360 g/L clomazone @ 1.5 l) | 90 |

From the above table it is evident that 90% to 93% of monocot weed control was observed after the application of D-napropamide and combination of dimethachlor+Clomazone (1.5 L/ha).

We claim:

1. A method of controlling a weed infestation at a locus, comprising the step of treating said locus with an herbicidally effective amount an herbicide formulation consisting essentially of:
    at least one agronomically acceptable excipient; and
    an herbicide composition consisting of D-Napropamide and an additional herbicide, wherein said additional herbicide is selected from the group consisting of Benzamide, Benzothiazolone, Carbamate, Carboxamide, Chloracetamide, Clomazone, Cyclodiene, Dinitroaniline, Organophosphate, Oxadiazolone, Oxyacetimide, Phenylpyridazine, Phenylurea, Pyridine, Quinoline, Triazine, Triazinone, and a combination thereof;
    wherein said herbicide formulation exhibits superior herbicidal efficacy compared with an equivalent formulation that uses Napropamide instead of D-Napropamide,
    wherein said herbicide formulation exhibits superior herbicidal efficacy compared with an equivalent formulation that uses L-Napropamide instead of D-Napropamide, and
    wherein said herbicide formulation demonstrates enhanced control in the growth of dicotyledonous weeds compared to monocotyledonous weeds.

2. The method of claim 1, wherein the Benzamide is propyzamide.

3. The method of claim 1, wherein the Benzothiazolone is benazolin.

4. The method of claim 1, wherein the Carbamate is carbetamide.

5. The method of claim 1, wherein the Carboxamide is diflufenican.

6. The method of claim 1, wherein the Chloracetamide, optionally in combination with Clomazone, is dimethachlor, metazachlor, metolachlor, S-metolachlor, or pethoxmide.

7. The method of claim 6, wherein the Chloracetamide is dimethachlor in combination with Clomazone.

8. The method of claim 6, wherein the Chloracetamide is metazachlor in combination with Clomazone.

9. The method of claim 6, wherein the Chloracetamide is S-metazachlor in combination with Clomazone.

10. The method of claim 1, wherein the Cyclodiene is flumetsulam.

11. The method of claim 1, wherein the Dinitroaniline is benfluraline, pendimethalin, or trifluralin.

12. The method of claim 1, wherein the Organophosphate is glufosinate.

13. The method of claim 1, wherein the Oxadiazolone is dimefuron.

14. The method of claim 1, wherein the Oxyacetimide is flufenacet.

15. The method of claim 1, wherein the additional herbicide is a combination of Oxyacetimide and Carbaxamide, and wherein said combination is flufenacet and diflufenican.

16. The method of claim 1, wherein the Phenylpyridazine is pyridate.

17. The method of claim 1, therein the Pyridine is clopyralid.

18. The method of claim 1, wherein the Quinoline is quinmerac.

19. The method of claim 1, wherein the Triazine is cyanazine or simazine.

20. The method of claim 1, wherein the Triazinone is metribuzin.

* * * * *